Figure 1:
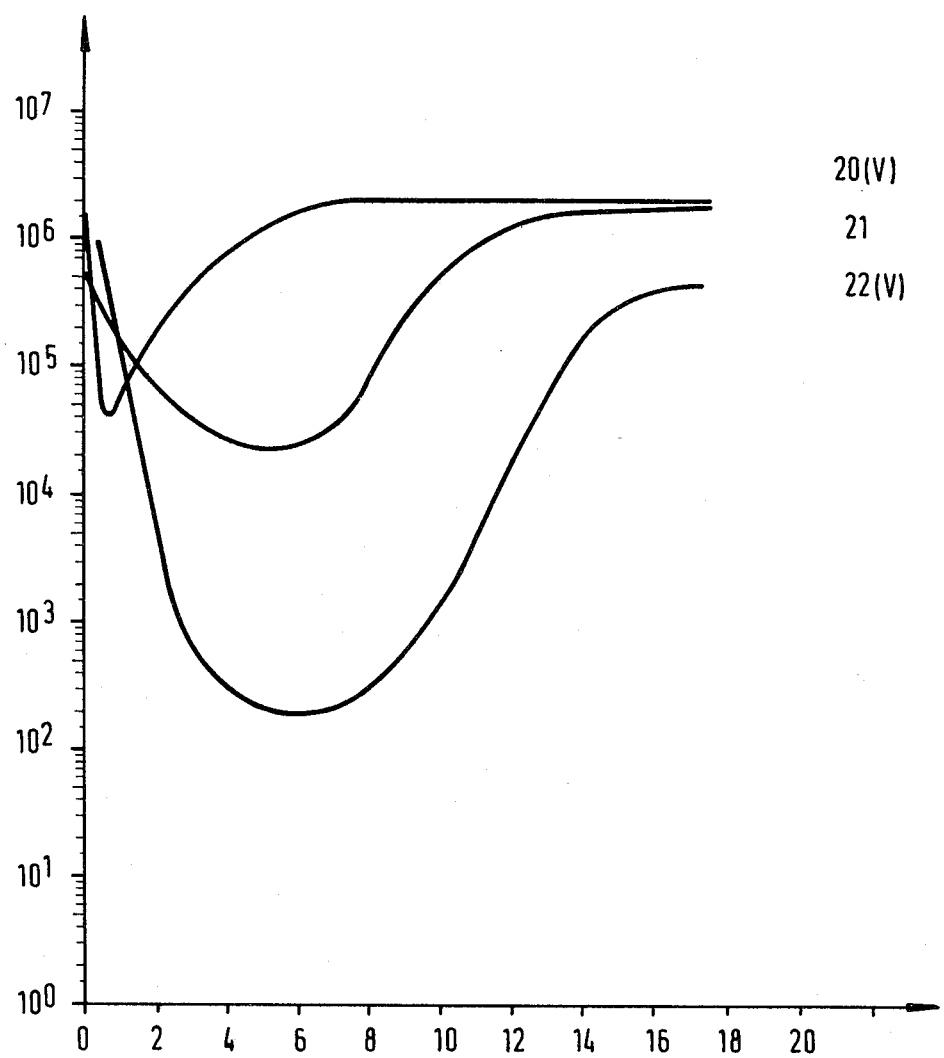

United States Patent [19]

Lorenz et al.

[11] 4,427,435
[45] Jan. 24, 1984

[54] USE OF IODOACETAMIDE AND AMINES FOR THE CONTROL OF HARMFUL ORGANISMS, AND AGENTS FOR SUCH CONTROL

[75] Inventors: Joachim Lorenz; Reinhardt Grade, both of Bensheim, Fed. Rep. of Germany

[73] Assignee: Ciba-Geigy Corporation, Ardsley, N.Y.

[21] Appl. No.: 272,425

[22] Filed: Jun. 10, 1981

[30] Foreign Application Priority Data

Jun. 12, 1980 [CH] Switzerland ........................ 4538/80

[51] Int. Cl.³ .................... A01N 33/04; A01N 43/64; A01N 37/18
[52] U.S. Cl. ........................................ 71/67; 424/249; 424/320; 424/325; 424/329
[58] Field of Search ................ 71/66, 67; 424/325, 424/320, 329, 249

[56] References Cited

U.S. PATENT DOCUMENTS 2,758,103  8/1956  Henson et al. .................. 260/29.7
4,070,400  1/1978  Dybas et al. .................. 260/570.5 P

FOREIGN PATENT DOCUMENTS 1419339  12/1975  United Kingdom .

OTHER PUBLICATIONS

Onozawa et al., Chem. Abstr. 86 (1977) 156979n.

Islam et al., Chem. Abstr. 89 (1978) 178266s.
A. Simek, et al. "Antimicrobially Active Substances", Folia Microbiologica 14, 508–510 (1969).
H. J. Hueck et al. "Bacteriostatic, Fungistatic, and Algistatic Activity of Fatty Nitrogen Compounds", Appl. Microbiology 14, 308–319 (1966).
A. T. Fuller "Antibacterial Action and Chemical Constitution in Long-Chain Aliphatic Bases", Biochem J. 36, 548–558 (1942).

*Primary Examiner*—Catherine L. Mills
*Attorney, Agent, or Firm*—Harry Falber

[57] ABSTRACT

A mixture of the compound of the formula I

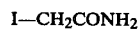

$$I-CH_2CONH_2 \qquad (I)$$

with amines or quaternary ammonium compounds is used to control, in particular, micro-organisms in water and in aqueous systems.

According to the invention, the compound of the formula I can also be employed without additional biocides for the control of micro-organisms in certain selected systems. These include, for example, swimming pools, ponds, cooling water, cutting and drilling oils, cellulose compositions, glues and starch pastes.

Agents which contain the biocide mixture or the compound of the formula I, together with auxiliaries, are claimed.

9 Claims, 3 Drawing Figures

USE OF IODOACETAMIDE AND AMINES FOR THE CONTROL OF HARMFUL ORGANISMS, AND AGENTS FOR SUCH CONTROL

The present invention relates to the control of harmful organisms in water and aqueous systems by the use of iodoacetamide or of mixtures of iodoacetamide and amines as active compounds.

The use of iodoacetamide as a biocide is already known from the following publications: Chem. Abstr. 86 (1977) 156979n, Chem. Abstr. 89 (1978) 178266s and German Auslegeschrift 1,018,174. The first of these publications relates to the use of iodoacetamide as a bactericide in oil-containing sizes for nylon fibres. However, these sizes are entirely anhydrous. The second literature reference relates to the use of iodoacetamide and chloroacetamide as agents to use against microorganisms in poultry raising. An exceptionally good action of iodoacetamide was not found in this context.

German Auslegeschrift No. 1,018,174 relates to the use of haloacetamides as active compounds to use against microorganisms in aqueous emulsion paints. Inter alia, it also describes a positive action of iodoacetamide, but this action does not stand out above that of the other haloacetamides.

We have found that iodoacetamide, both alone and in combination with amines, surprisingly shows a greater biological activity than other haloacetamides.

The present invention relates to the use of the compound of the formula I $$I-CH_2CONH_2 \qquad (I)$$

in combination with amines or quaternary ammonium compounds, for the control of harmful organisms in water or in aqueous systems.

Preferably, the concentration of the compound of the formula I is from 10 to 1,000 ppm, preferably from 30 to 300 ppm, and the concentration of the amine or of the quaternary ammonium compound is from 1 to 300 ppm, preferably from 5 to 30 ppm, in each case relative to the water or the aqueous system.

Suitable amines for the use according to the invention are virtually all known amines and corresponding quaternary ammonium compounds, including in particular those biocidal amines which have already been comprehensively described in the literature.

In this respect, reference may particularly be made to the following publications: A. Simek et al. "Antimicrobially active substances", Folia Microbiologica 14, 508–510 (1969); H. J. Hueck et al. "Bacteriostatic, fungistatic, and algistatic activity of fatty nitrogen compounds", Appl. Microbiology 14, 308–319 (1966); A. T. Fuller "Antibacterial action and chemical constitution in long-chain aliphatic bases", Biochem J. 36, 548–558 (1942); German Pat. No. 2,247,369 and U.S. Pat. No. 4,070,400.

In principle, primary, secondary and tertiary amines can be used.

The amines employed are preferably aliphatic or predominantly aliphatic.

Polyfunctional aliphatic amines, especially diprimary amines having 2 to 20 carbon atoms in the alkylene radical separating the two amino groups, are especially preferred.

Typical examples of this category are amines of the formula II

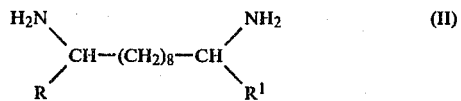

in which R and $R^1$ are identical or different and each is a straight-chain or branched alkyl radical having a total of 1 to 14 carbon atoms or is an unsubstituted or alkyl-substituted cycloalkyl radical having a total of 3 to 12 carbon atoms.

Such amines and their preparation are described, for example, in U.S. Pat. No. 4,100,111.

The following compounds are some examples of the numerous amines of the formula II: 9,18-diaminohexacosane, 8,17-diaminotetracosane, 7,16-diaminodocosane, 2,11-diaminododecane, 3,12-diaminotetradecane and 4,13-diaminohexadecane.

Other amines suitable for use in the combination according to the invention are alkyl-1,3-propylenediamines, in which the alkyl radical is, for example, lauryl, or is the mixture of alkyl radicals (mean $C_{12}H_{25}$) present in (so-called) coconut amine.

Cyclic amines are also suitable, for example hexahydro-s-triazines, which can additionally be substituted at the nitrogen, as in, for example, 1,3,5-trishydroxyethylene-hexahydro-s-triazine or 1,3,5-tris-ethylhexahydro-s-triazine.

According to the invention, both the free amines and the salts thereof can be used, for example the salts with the following inorganic or organic acids: hydrochloric acid, phosphoric acid, phosphorous acid, carbonic acid, sulfuric acid, sulfurous acid, acetic acid, citric acid and formic acid.

The agents used according to the invention for the control of harmful organisms are highly active against harmful micro-organisms. Specific examples of organisms which can be controlled by the use according to the invention are bacteria, fungi, yeasts and algae.

The preferred use according to the invention is for the control of harmful organisms in stagnant and running waters, such as swimming pools and ponds, and especially in cooling water circuits, and also for the control of micro-organisms in natural and synthetic industrial aqueous materials. Examples of the latter are cutting and drilling oils, paper and cellulose compositions, aqueous dispersion paints, agrochemicals, glues and starch pastes.

Especially in the case of the control of harmful organisms in cooling water, conventional auxiliaries can additionally be employed in the use according to the invention, for example corrosion inhibitors, anti-furring agents, water softeners, masking agents, for example polymeric phosphites, phosphates, amides of phosphoric acid, phosphonic acids, polymeric carboxylic acids, derived, for example, from acrylic acid or maleic acid, their anhydrides or salts, and other additives.

The combination of the compound of the formula I with amines results in a pronounced synergistic effect in respect of activity. This effect is that mixing of the active compounds results in very rapid destruction of the harmful organisms and that the inhibition of growth is sustained for an astonishingly long period, for example for more than 18 days.

The invention also provides the use of the compound of the formula I alone, i.e. without addition of an amine, for control of harmful organisms in stagnant and running waters, such as swimming pools and ponds and especially in cooling water circuits, as well as for control of harmful organisms in cutting and drilling oils, in paper and cellulose compositions, in agrochemicals, in glues and in starch pastes.

The compound of the formula I is employed, in such applications, in concentrations of 10 ppm or more, preferably of 25 to about 1,000 ppm.

The method of use according to the invention is that the agent used against harmful organisms (iodoacetamide alone, or in combination with amines) is dissolved or dispersed in the water or aqueous material to be protected, and is then allowed to act for a sufficiently long period. In certain cases, however, it is also possible to add a larger amount of the particular pest control agent than is necessary per se for dissolving and/or dispersing, or to add the agent very cautiously, so that over-rapid solution or emulsification is initially avoided. Such methods have the effect that particles of large volume, or large drops, are also present in the material to be protected. This can be of advantage if a depot action of the iodoacetamide or of the combination of the latter with amines is important.

In dissolving the active compounds for the use according to the invention, liquid, pasty or solid formulations (agents) can serve as the starting material. Such formulations can be, for example, suspensions, emulsions and solutions in organic or inorganic solvents.

Accordingly, the invention also provides agents for the control of micro-organisms, which contain a mixture (R) of the compound of the formula I with amines or quaternary ammonium compounds, together with an auxiliary suitable for agents for the control of microorganisms, the concentration of the mixture (R) being 0.1 to 10, preferably 0.5 to 5, % by weight of the complete agent.

In general, the following auxiliaries are particularly required for the preparation of the agents or formulations for use against harmful organisms: carriers, extenders, emulsifiers, humectants, fixing agents and surfactants. Suitable carriers may be solid or liquid and are, for example, clay, kaolin, talc, diatomaceous earth, silica, calcium carbonate, benzene, alcohols, xylene, polyols, polyethylene oxide adducts, methylnaphthalene, dimethylformamide, diethylsulfoxide, animal and vegetable oils, fatty acids and their esters and various surfactants.

The invention also provides agents for the control of micro-organisms, which contain the compound of the formula I together with an auxiliary suitable for agents for the control of micro-organisms, the concentration of the compound of the formula I being 0.1 to 10, preferably 0.5 to 5, % by weight of the complete agent.

EXAMPLE 1

Determination of the minimum inhibitory concentration (MIC) of iodoacetamide against algae Cultures of the following different strains of algae:

| | |
|---|---|
| Oscillatoria geminate | DSM 1459-8 |
| Nostoc spec. | DSM 1453-7 |
| Phormidium foveolarum | DSM B 1462-1 |
| Anacystis nidulans | DSM L 1402-1 |
| Chlorella vulgaris | DSM 211-11 a |
| Chlorella pyrenoidosa | DSM 211-3 m |
| Scenedesmus spec. | DSM 276-7 |
| Ulothrix subtilissima | DSM 384-1 |

-continued

| | |
|---|---|
| Tribonema aequale | DSM 880-1 | are grown in nutrient media for algae for 14 days and then diluted 1/100 or 1/200 with nutrient medium. The suspensions are dripped onto algae agar which contains the biocide in various concentrations. After incubation for 14 days at room temperature under alternation of 14 hours of light with 10 hours of darkness, the cultures were assessed in respect of growth. At the same time, the algae present in the algae nutrient medium±biocide in the flask were incubated on a shaker at 18° C. under alternation of 14 hours of light with 10 hours of darkness. Results:

TABLE 1

MIC determination (concentration investigated: 3, 10 and 30 mg/l)

| Species of alga | MIC (mg/l) in the agar | MIC (mg/l) in the liquid culture |
|---|---|---|
| Oscillatoria geminata | 3 | 3 |
| Nostoc spec. | 3 | 3 |
| Phormidium foveolarum | 3 | 3 |
| Anacystis nidulans | 3 | 3 |
| Chlorella vulgaris | 10 | 10 |
| Chlorella pyrenoidosa | 10 | 10 |
| Scenedesmus spec. | 3 | 3 |
| Ulothrix subtilissima | 3 | 3 |
| Tribonema aequale | 3 | 3 |

Table 1 shows that iodoacetamide inhibits the growth of the algae even at low concentration.

EXAMPLE 2

Determination of the MIC of iodoacetamide against bacteria

The overnight cultures of the various bacterial strains, grown in casein-peptone-broth (Merck) are each diluted 1/1,000 in saline. This suspension is either dripped onto casein agar (agar incorporation test), or added in sufficient amount to casein-peptone-broth (±biocide) that the bacteria are again diluted 1/100 (final dilution $10^{-5}$). After an incubation of 24 hours at 30° C. in an incubation cabinet or in a shaken waterbath, the growth of the agar, and the turbidity in the flask, are evaluated. Results:

TABLE 2

MIC determination (concentration investigated: 1, 3, 10, 30, 100 and 300 mg/l)

| Species of bacteria | | MIC (mg/l) in the agar | MIC (mg/l) in the liquid culture |
|---|---|---|---|
| Bacillus cereus var. mycoides | DSM 299 | 30 | 30 |
| Bacillus subtilis | ATCC 6051 | 100 | 10 |
| Streptomyces griseus | ATCC 23345 | 100 | 30 |
| Staphylococcus aureus | ATCC 6538 P | 30 | 10 (30) |
| Pseudomonas aeruginosa | DSM 288 | 30 | 30 (10) |
| Enterobacter aerogenes | ATCC 13048 | 100 | 30 |
| Serratia marcescens | ATCC 13880 | 100 | 30 |
| Alcaligenes denitrificans | ATCC 15173 | 30 | 10 |
| Escherichia coli | ATCC 4157 | 30 | 30 |
| Proteus vulgaris | ATCC 13315 | 100 | 30 |
| Pseudomonas oleovorans | ATCC 8062 | 30 | 10 |

As can be seen from Table 2, iodoacetamide is an excellent agent for inhibiting bacterial growth. A concentration of 30 ppm suffices to inhibit the growth, in liquid culture, of the entire spectrum of bacteria tested.

EXAMPLE 3

Determination of the MIC of iodoacetamide against the anaerobic bacterium Desulfovibrio disulfuricans DSM 642

This is carried out by the method of Merck, Mikrobiologisches Handbuch (Microbiological Handbook), germ count agar for sulfate-reducing bacteria (API). Results Iodoacetamide exhibits an excellent action against the anaerobic bacterial strain Desulfovibrio disulfuricans. This bacterial strain is important for such fields of application as cooling water circuits, drilling and cutting oils, secondary oil production and others. A concentration of 10 ppm of the product suffices (the concentrations investigated being 10, 30 and 100 mg/l) to inhibit the growth of the bacterial strain.

EXAMPLE 4

Determination of the MIC of iodoacetamide against fungi

The investigation is carried out by the agar incorporation test in malt-extract agar, with 6 different fungi and 2 yeasts.

For inoculation, a spore suspension is used in the case of each of the fungi, and a 1/1,000 diluted overnight culture in the case of the yeasts. The plates are incubated for 7 days at 28° C. Results

TABLE 3

MIC determination against fungi (concentration investigated: 10, 50 and 100 mg/l)

| Strain | | MIC (mg/l) |
|---|---|---|
| Aspergillus niger | ATCC 9642 | 50 |
| Aspergillus phoenicis | IMB 7188 | 50 |
| Penicillium funiculosum | IMB 11401 | 50 |
| Alternaria alternata | IMB 12090 | 50 |
| Cladosporium cladosporioides | IMB 11993 | 50 |
| Candida albicans | ATCC 752 | 50 |
| Endomyces geotrichum | ATCC 22600 | 50 |
| Aureobasidium pullulans | IMB 8624 | 50 |

Iodoacetamide is thus also an excellent fungicide.

EXAMPLES 5 TO 9

Destruction of Pseudomonas aeruginosa

The overnight culture of the bacterial strain Pseudomonas aeruginosa DSM 288, grown in casein-peptone-broth, is diluted 1/1,000 in saline. This suspension is further diluted 1/100 in tyrode (final dilution $10^{-5}$) and the culture is incubated for 5 hours at 30° C. in a shaken waterbath (±100 mg/l of biocide). 5 μl is then taken from the samples and dripped onto casein-peptone agar. After renewed incubation at 30° C., for 24 hours, the growth is examined visually. Results

TABLE 4

Destruction of Pseudomonas aeruginosa (100 mg/l)

| Example | Compound | Destruction (no growth on the plate) |
|---|---|---|
| 5 (V) | Ethyl iodoacetate | + |
| 6 (V) | Iodoacetic acid | − |
| 7 (V) | Chloroacetic acid | − |
| 8 | Iodoacetamide | + |
| 9 (V) | Chloroacetamide | − |

+ = destruction.
− = no destruction in 5 h with 100 mg/l in tyrode.
(V) = comparative example.

EXAMPLES 10 TO 14

MIC determination against bacteria

The test is carried out as described in Example 2. The minimum inhibitory concentration is determined in casein-peptone-broth against the following strains of bacteria:

| 7 | Pseudomonas aeruginosa | DSM 288 |
|---|---|---|
| 10 | Enterobacter aerogenes | ATCC 13048 |
| 11 | Alcaligenes denitrificans | ATCC 15173 |
| 8 | Serratia marcescens | ATCC 13880 |
| 13 | Proteus vulgaris | ATCC 13315 |
| 2 | Bacillus subtilis | ATCC 6051 |

Results

TABLE 5

MIC determination (concentrations investigated: 30 and 100 mg/l)

| Example | Compound/bacterial strain | 7 | 10 | 11 | 8 | 13 | 2 |
|---|---|---|---|---|---|---|---|
| 10 (V) | Ethyl iodoacetate | 100 | 30 | 30 | 30 | 30 | 30 |
| 11 (V) | Iodoacetic acid | >100 | >100 | >100 | >100 | 100 | 100 |
| 12 (V) | Chloroacetic acid | >100 | >100 | >100 | >100 | >100 | >100 |
| 13 | Iodoacetamide | 30 | 30 | 30 | 30 | 30 | 30 |
| 14 (V) | Chloroacetamide | >100 | >100 | >100 | >100 | >100 | >100 |

((V) = comparative example)

The only compound which has a comparable action to that of iodoacetamide is ethyl iodoacetate. This compound has the disadvantage, however, that it is volatile and strongly lachrymatory. All other compounds investigated are insufficiently active.

Bromoacetamide, not included in Table 5, also shows the same unfavourable properties (strong lachrymatory action and volatility) as ethyl iodoacetate.

EXAMPLE 15

Action of iodoacetamide in drilling and cutting oils

The investigation is carried out with the following cooling lubricant: BP Fedaro SB-EP 5520 ®, a partially synthetic drilling oil having an oil content of less than 60% and containing, inter alia, high-pressure additives and non-ionic emulsifiers. A test apparatus according to Hill, O. Gibbon and P. Davies, as described in a publication "Biocides for use in oil emulsions", in Tribology International, June 1976, is used.

The concentrate is diluted 1/20 with $H_2O$ and the lubricant is then inoculated with a mixed culture of bacteria and yeasts (final dilution 1/1,000).

The mixed culture used for inoculation consists of the following strains (1:1:1 etc. ratio of the overnight cultures):

| | |
|---|---|
| Escherichia coli | ATCC 4157 |
| Staphylococcus aureus | ATCC 6538 P |
| Pseudomonas aeruginosa | DSM 288 |
| Enterobacter aerogenes | ATCC 13048 |
| Proteus vulgaris | ATCC 13315 |
| Pseudomonas oleovorans | ATCC 8062 |
| Candida albicans | ATCC 752 |
| Endomyces geotrichum | ATCC 22600 |

To evaluate the experiment, samples were taken before each weekly inoculation and the germ count was determined by diluting and smearing on casein-peptone agar.

Results

TABLE 6

Action of 500 ppm of Iodoacetamide in BP Fedaro SB-EP 5520

| Week | Date | Control (germs/ml) | Iodoacetamide (germs/ml) |
|---|---|---|---|
| 0 20 h | 12.10.78 | $3.1 \times 10^7$ | $4.3 \times 10^2$ |
| 1 | 17.10.78 | $3.3 \times 10^8$ | $4.0 \times 10^1$ |
| 2 | 24.10.78 | $1.5 \times 10^8$ | $2.0 \times 10^3$ |
| 3 | 31.10.78 | $1.3 \times 10^8$ | $1.0 \times 10^3$ |
| 4 | 7.11.78 | $2.8 \times 10^8$ | $10^1$ |
| 5 | 14.11.78 | $1.8 \times 10^8$ | $10^1$ |
| 6 | 21.11.78 | $2.6 \times 10^8$ | $10^1$ |
| 7 | 28.11.78 | $1.6 \times 10^8$ | $10^1$ |
| 8 | 5.12.78 | $1.2 \times 10^8$ | $10^1$ |
| 9 | 12.12.78 | $7.9 \times 10^7$ | $4 \times 10^2$ |
| 10 | 19.12.78 | $3.1 \times 10^8$ | $9 \times 10^2$ |
| 11 | 28.12.78 | | $10^2$ |
| 12 | 4. 1.79 | | $1.8 \times 10^3$ |

As can be seen from Table 6, 500 ppm of iodoacetamide are highly effective over 12 weeks in the test apparatus. No corrosion of the coarse steel turnings present in the test apparatus was found.

EXAMPLES 16 TO 19

Comparative investigation of the activity of iodoacetamide and Grotan BK ® in drilling and cutting oils (Grotan BK ® is the registered trademark of Schülke u. Meier for 1,3,5-tris-hydroxyethylene-hexahydro-triazine)

The investigation is carried out with the following two cooling lubricants:

(a) BP Fedaro M ®, a conventional drilling oil, consisting of mineral oil, anti-corrosion additives and stabilising additives, and anionic emulsifiers.

(b) BP Fedaro SB-EP 5520 ®, a partially synthetic drilling oil having an oil content of less than 60% and containing, inter alia, high-pressure additives and non-ionic emulsifiers.

The two lubricants (concentrates diluted 1/20 with H₂O) are inoculated with a bacteria/yeast mixed culture (final dilution 1/100), the biocides are added at various concentrations and the tubes are incubated on a roller apparatus at room temperature. They are each reinoculated at the end of each week's incubation. Before inoculation, samples are taken in each case and diluted 1/1,000 in saline. After dripping 5 μl (2×) onto the casein agar plates and incubating these for 3 days at 30° C., the growth is evaluated. The mixed culture used for the inoculation consists of the following strains (1:1:1 etc. ratio of the overnight cultures):

| | |
|---|---|
| Escherichia coli | ATCC 4157 |
| Bacillus subtilis | ATCC 6051 |
| Staphylococcus aureus | ATCC 6538 P |
| Enterobacter aerogenes | ATCC 13048 |
| Proteus vulgaris | ATCC 13315 |
| Pseudomonas aeruginosa | DSM 288 |
| Pseudomonas oleovorans | ATCC 8062 |
| Candida albicans | ATCC 752 |
| Endomyces geotrichum | ATCC 22600 |

Results

TABLE 7

Action in a BP Fedaro EP 5520

| Initial concentration (mg/l) | Example 16 (comparative experiment Grotan BK ®) | | | | | | | | | | | | | | | Example 17 Iodoacetamide | | | | | | | | | | | | | | |
|---|---|---|---|---|---|---|---|---|---|---|---|---|---|---|---|---|---|---|---|---|---|---|---|---|---|---|---|---|---|---|
| weeks → | 1 | 2 | 3 | 4 | 5 | 6 | 7 | 8 | 9 | 10 | 11 | 12 | 13 | 14 | 15 | 1 | 2 | 3 | 4 | 5 | 6 | 7 | 8 | 9 | 10 | 11 | 12 | 13 | 14 | 15 |
| 25 | + | | | | | | | | | | | | | | | − | + | | | | | | | | | | | | | |
| 50 | + | | | | | | | | | | | | | | | − | − | + | | | | | | | | | | | | |
| 100 | − | + | | | | | | | | | | | | | | − | − | − | − | + | | | | | | | | | | |
| 250 | − | − | − | + | | | | | | | | | | | | − | − | − | − | − | − | − | − | (−) | + | | | | | |
| 500 | − | − | − | − | − | − | − | + | | | | | | | | − | − | − | − | − | − | − | − | − | − | − | − | − | − | − |
| 1000 | − | − | − | − | − | − | − | − | − | − | + | | | | | − | − | − | − | − | − | − | − | − | − | − | − | − | − | − |

TABLE 8

Action in BP Fedaro M

| Initial concentration (mg/l) | Example 18 (comparative experiment Grotan BK ®) | | | | | | | | | | | | | | | Example 19 Iodoacetamide | | | | | | | | | | | | | | |
|---|---|---|---|---|---|---|---|---|---|---|---|---|---|---|---|---|---|---|---|---|---|---|---|---|---|---|---|---|---|---|
| weeks → | 1 | 2 | 3 | 4 | 5 | 6 | 7 | 8 | 9 | 10 | 11 | 12 | 13 | 14 | 15 | 1 | 2 | 3 | 4 | 5 | 6 | 7 | 8 | 9 | 10 | 11 | 12 | 13 | 14 | 15 |
| 25 | + | | | | | | | | | | | | | | | − | + | | | | | | | | | | | | | |
| 50 | + | | | | | | | | | | | | | | | − | − | + | | | | | | | | | | | | |
| 100 | + | | | | | | | | | | | | | | | − | − | − | − | (−) | + | | | | | | | | | |

TABLE 8-continued

Action in BP Fedaro M

| Initial concentration (mg/l) | Example 18 (comparative experiment Grotan BK ®) 1 2 3 4 5 6 7 8 9 10 11 12 13 14 15 weeks | Example 19 Iodoacetamide 1 2 3 4 5 6 7 8 9 10 11 12 13 14 15 weeks |
|---|---|---|
| 250 | − + | − − − − − − − − − − − − (+) + |
| 500 | − − − − − + | − − − − − − − − − − − − − − − |
| 1000 | − − − − − − − + | − − − − − − − − − − − − − − − | weekly inoculation, single dose
+ = growth on the agar plate, product inactive
− = no growth on the plate, bacteria have been destroyed Tables 7 and 8 show the superior action of iodoacetamide compared to Grotan BK ®.

EXAMPLE 20–24

Investigation of the activity of various biocides in model circulation systems

The model circulation systems, standing by the window in a closed room, consist of the following:

(a) a plastic barrel having a volume of 113 liters
(b) a Siemens pump (21 l/min at 3 m delivery height)
(c) a cooling tower with Oregon pine, Oregon pine heartwood, oak, spruce, asbestos cement and PVC panels
(d) a plastic sheet over the cooling tower, to avoid splashed water.

The system is topped up daily to compensate for evaporated water (about 1–2 liters/24 h). The model circulation systems are inoculated on Friday with the following cultures:

| 1. 14 day old algae cultures (5 ml each) of | |
|---|---|
| Oscillatoria geminata | DSM 1459-8 |
| Nostoc spec. | DSM 1453-7 |
| Phormidium foveolarum | DSM B 1462-1 |
| Anacystis nidulans | DSM L 1402-1 |
| Chlorella vulgaris | DSM 211-11 a |
| Chlorella pyrenoidosa | DSM 211-3 m |
| Scenedesmus spec. | DSM 276-7 |
| Ulothrix subtilissima | DSM 384-1 |
| Tribonema aequale | DSM 880-1 |

| 2. 1 ml each of the overnight cultures of the following bacterial strains | |
|---|---|
| 4 Bacillus cereus var. mycoides | DSM 299 |
| 2 Bacillus subtilis | ATCC 6051 |
| 20 Streptomyces griseus | ATCC 23345 |
| 6 Staphylococcus aureus | ATCC 6538 P |
| 7 Pseudomonas aeruginosa | DSM 288 |
| 10 Enterobacter aerogenes | ATCC 13048 |
| 8 Serratia marcescens | ATCC 13880 |
| 11 Alcaligenes denitrificans | ATCC 15173 |
| 1 Escherichia coli | ATCC 4157 |
| 13 Proteus vulgaris | ATCC 13315 |

After incubation for 72 hours at room temperature, the biocide is added, as a single shot, on Monday.

Example 20 (V): 10 ppm of active compound of a 10% formulation of N-(coconut alkyl)-1,3-propylenediamine in ethylene glycol monomethyl ether.

Example 21: 30 ppm of iodoacetamide active compound = 36% formulation in ethylene glycol monomethyl ether.

Example 22 (V): 10 ppm of Kathon WT ® active compound = 14% formulation of an isothiazoline mixture in water.

Example 23: 10 ppm of active compound of a formulation according to Example 20(V) + 30 ppm of iodoacetamide active compound.

Example 24 (V): 100 ppm of active compound according to Example 20 (V) + 10 ppm of Kathon WT ® active compound.

Example 25 (V): 10 ppm of active compound of a 2% formulation of 7,16-diaminodocosane in ethylene glycol monomethyl ether.

Example 26: 10 ppm of active compound of a formulation according to Example 25 (V) + 30 ppm of iodoacetamide active compound.

Example 27 (V): 30 ppm of active compound Kemamine BAC ® = 50% aqueous solution of a mixture of alkylbenzyldimethylammonium chlorides.

Example 28: 30 ppm of active compound of a formulation according to Example 27 (V) + 30 ppm of iodoacetamide active compound.

The experiment is evaluated by determining the germ count by dilution and preparing a smear.

The germ count is determined before addition of the biocide and 1 hour and 5 hours after addition, as well as once daily (except for Saturday and Sunday).

The formation of slime on the various woods, the change in the quality of the water and any frothing are observed visually.

Figure 2:
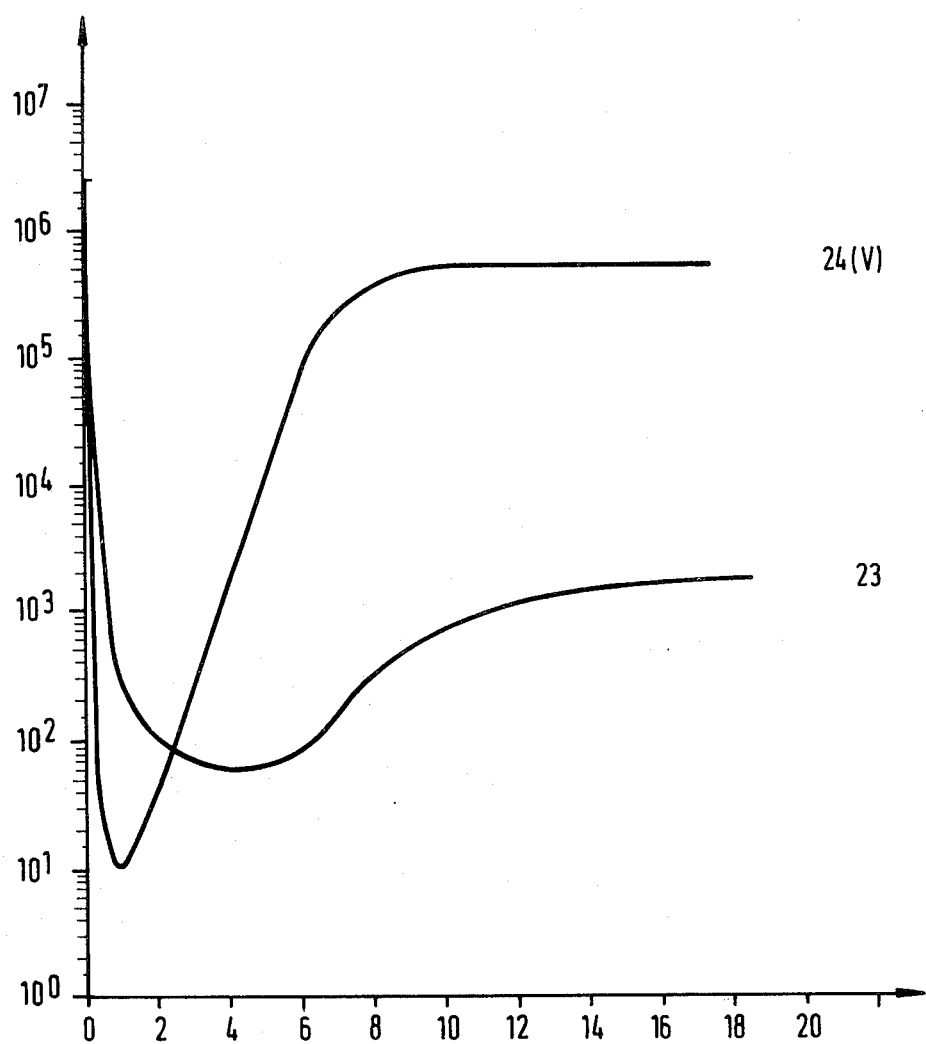
Figure 3:
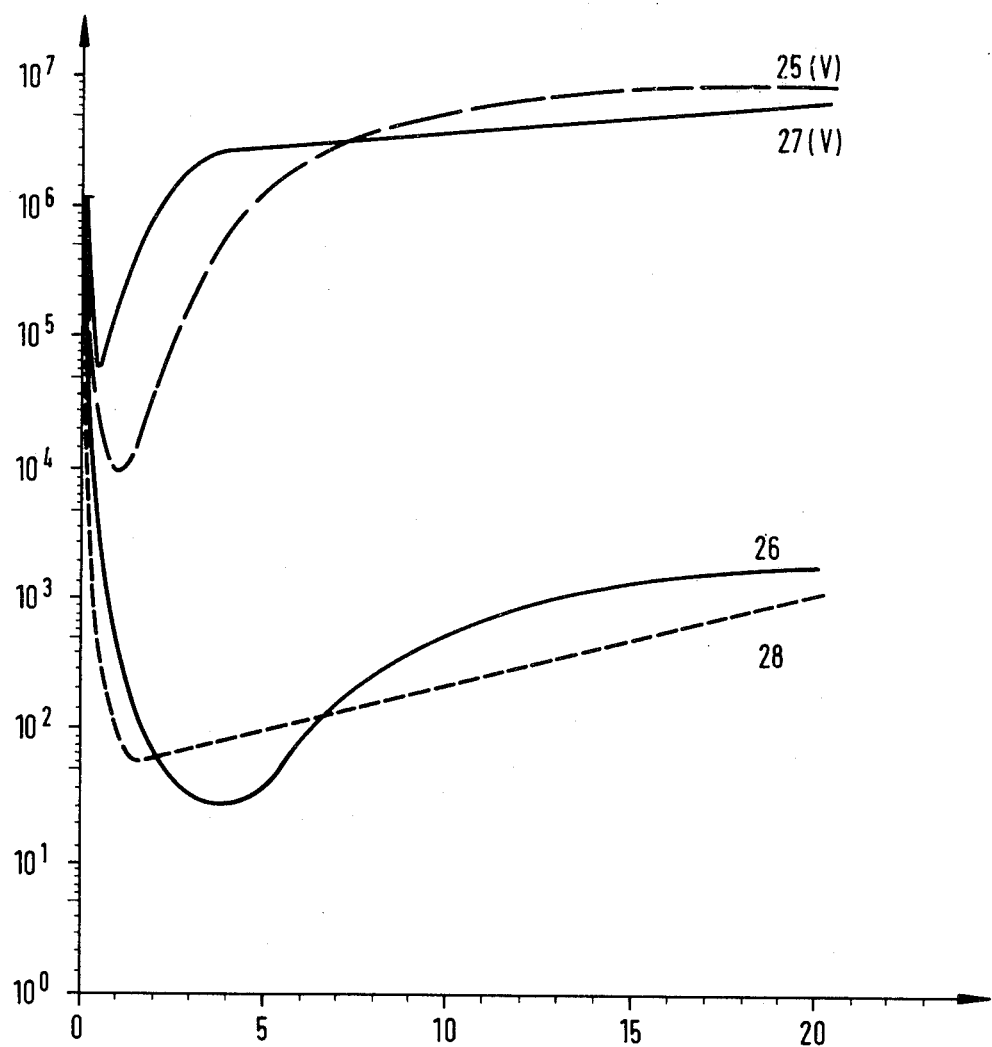

The results of the experiments are illustrated in FIGS. 1 to 3 and are discussed below.

As can be seen from FIGS. 1 and 3, the bacteria are rapidly destroyed by addition of a diamine or of a quaternary ammonium compound (Example 20 (V), Example 25 (V), Example 27 (V)). The activity of the product however disappears within a few hours, so that the bacteria can multiply again to their original germ count.

Kathon WI ® (Example 22 (V)) is active in this medium for more than 9 days, before the germ count rises again. In the first 6 days of the treatment, destruction of the bacteria is observed.

The germ count of the water treated with iodoacetamide (Example 21) decreases in the first 5 days. After 7 days, iodoacetamide, at the tested concentration, is no longer active in this medium and the bacteria multiply again to their original germ count.

With the combination (Example 24 (V)) 99.99% destruction of the bacteria can again be attained. However, the bacterial count begins to rise again after 1 day, though Kathon WT ® should prevent the growth, as can indeed be seen with Kathon WT ® alone in FIG. 1, Example 22 (V). This rise in the germ count in spite of the presence of Kathon WT ® (100 ppm initially) can only mean that the growth-inhibiting action of this biocide is annulled by the simultaneous addition of alkyldiamine. Accordingly, a synergistic effect cannot be achieved in every case by mixing an inhibiting biocide with a destroying biocide.

The best combination of biocides for keeping the germ count in a closed circulation system as low as possible for a long time is a combination of iodoacetamide with a diamine (as in Example 23 and in Example 26) or with a quaternary ammonium compound (as in Example 28). A single dose of these combinations suffices to keep the germ count below about $10^3$ germs/ml for more than 18 days and thereby to suppress slime formation entirely.

In contrast to the previously described combination of the isothiazolone mixture with amine (Example 24 (V)), the combination of iodoacetamide with a diamine or a quaternary ammonium compound (Example 23, Example 26, Example 28) shows a genuine synergistic effect.

Iodoacetamide alone has a growth-inhibiting action for 5–7 days; a diamine destroys most of the bacteria but the surviving bacteria grow again, within as little as 2–3 days, to their original germ count.

The combination of these two products effects a rapid destruction of the germs and growth inhibition of the surviving germs for a long period.

The duration of this growth inhibition, namely more than 18 days, was not to be expected. The further inhibition of the growth of the bacteria after 7 days and up to more than 18 days represents a synergistic effect.

What is claimed is:

1. A method for combatting harmful bacteria, fungi, yeasts or algae present in an aqueous medium which comprises adding to said medium an effective combatting amount of a combination of from 30–300 ppm of iodoacetamide and from 5–30 ppm of a microbiocidal amine selected from the group consisting of aliphatic amines, hexahydro-s-triazines amines and the corresponding quaternary ammonium compounds, said concentration being based on the aqueous medium.

2. The method according to claim 1, wherein aliphatic or predominantly aliphatic amines are employed.

3. The method according to claim 1, wherein polyfunctional aliphatic amines are employed.

4. The method according to claim 3, wherein an alkyl-1,3-propylenediamine in which the alkyl radical is the mixture of alkyl radicals (mean $C_{12}H_{25}$) present in coconut amine, is employed.

5. The method according to claim 1, wherein said aqueous medium is stagnant or running water or a natural or synthetic industrial aqueous material selected from the group consisting of cutting and dispersion paints, agrochemicals, glues and starch pastes.

6. The method of claim 3, wherein said polyfunctional aliphatic amine is a di-primary amine having 2 to 20 C atoms in the alkylene radical separating the two amino groups.

7. The method of claim 4, wherein said propylenediamine is a monoalkyl-1,3-propylenediamine.

8. The method according to claim 6, wherein an amine of the formula II

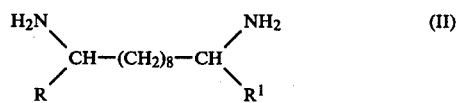

in which R and $R^1$ are identical or different and each is a straight-chain or branched alkyl radical having a total of 1 to 14 carbon atoms or is an unsubstituted or alkyl-substituted cycloalkyl radical having a total of 3 to 12 carbon atoms, is employed.

9. A composition for combatting harmful bacteria, fungi, yeasts or algae present in an aqueous medium which comprises from 0.1–10%, by weight, of a combination of from 30–300 ppm of iodoacetamide and from 5–30 ppm of a microbiocidal amine selected from the group consisting of aliphatic amines, hexahydro-s-triazines amines and the corresponding quaternary ammonium compounds, together with a suitable auxiliary ingredient therefor.

* * * * *